United States Patent [19]
Kudo et al.

[11] Patent Number: 5,152,928
[45] Date of Patent: Oct. 6, 1992

[54] SURFACTANT AND METHOD FOR PRODUCING THE SAME

[75] Inventors: Satoshi Kudo; Eriko Nishi, both of Tokyo, Japan

[73] Assignee: Kabushiki Kaisha Yakult Honsha, Tokyo, Japan

[21] Appl. No.: 623,416

[22] PCT Filed: Mar. 30, 1990

[86] PCT No.: PCT/JP90/00432

§ 371 Date: Dec. 12, 1990

§ 102(e) Date: Dec. 12, 1990

[87] PCT Pub. No.: WO90/11823

PCT Pub. Date: Oct. 18, 1990

[30] Foreign Application Priority Data

Apr. 13, 1989 [JP] Japan .................. 1-091840

[51] Int. Cl.$^5$ ............................................. B01F 17/00
[52] U.S. Cl. ........................................ 252/351; 252/306; 252/312; 252/318; 252/314; 514/78; 424/450; 554/79; 536/117
[58] Field of Search ............... 252/312, 318, 306, 351, 252/364; 514/78; 260/403; 424/450

[56] References Cited

U.S. PATENT DOCUMENTS

| | | | |
|---|---|---|---|
| 4,849,137 | 7/1989 | Kobayashi | 260/403 |
| 4,923,854 | 5/1990 | Tilcock et al. | 514/78 |
| 4,960,814 | 10/1990 | Wu et al. | 524/312 |
| 5,025,004 | 6/1991 | Wu et al. | 514/165 |
| 5,043,376 | 8/1991 | Sharma et al. | 524/376 |

FOREIGN PATENT DOCUMENTS

| | | |
|---|---|---|
| 33-51853 | 3/1958 | Japan. |
| 61-88886 | 5/1986 | Japan. |
| 62-205788 | 9/1987 | Japan. |
| 62-262998 | 11/1987 | Japan. |
| 63-42691 | 2/1988 | Japan. |
| 63-91306 | 4/1988 | Japan. |
| 63-245684 | 10/1988 | Japan. |
| 63-279753 | 11/1988 | Japan. |

Primary Examiner—Richard D. Lovering
Assistant Examiner—N. Bhat
Attorney, Agent, or Firm—Fleit, Jacobson, Cohn, Price, Holman & Stern

[57] ABSTRACT

Surfactant containing one or more of lysophospholipid represented by general formula;

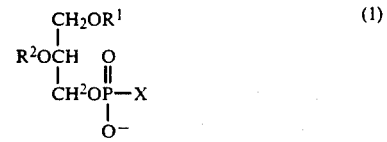

[wherein $R^1$ and $R^2$ represent hydrogen atom or the acyl residue of fatty acid, but either one of $R^1$ and $R^2$ is hydrogen atom, the other being acyl group. X represents an organic group remaining after removing one hydrogen atom of an optional hydroxyl group of polyhydric alcohol therefrom] and the method for producing the same are described.

8 Claims, No Drawings

SURFACTANT AND METHOD FOR PRODUCING THE SAME

FIELD OF THE INVENTION

The present invention relates to a surfactant and the method for producing the same.

BACKGROUND ART

There have been generally used soybean lecithin, sucrose fatty acid ester, glycerin fatty acid ester, sorbitan fatty acid ester, propylene glycol fatty acid ester as the food surfactant, conventionally. Among them, soybean lecithin has been modified for the objective specifically to improve the HLB value thereof. That is, although soybean lecithin is excellent in terms of safety, its HLB value is as low as 3 to 8, which results in the disadvantages not only that the lecithin is difficult to be dissolved in water but that its surfacing action is exhibited only within a limited range, involving the limited use thereof. For that reason, investigation has been carried out over the modification of soybean lecithin in order to provide it with an HLB value approximately at the same degree of that of other higher HLB emulsifiers.

Soybean lecithin has been modified by a variety of means including transphosphatidylation (Japanese Patent Laid-open No.61-199749), acetylation, hydroxylation, hydrolysis of fatty acid moiety, owing to the easy modifiable molecular structure thereof. Consequently, transfer lecithin is in practical use on confirmation that transfer lecithin in which the choline bonded with the phosphoryl group of lecithin is substituted with polyhydric alcohol such as glycerol, glucose, sorbitol and the like, has an HLB value of about 15.

However, some other surfactants produced by chemical synthesis, for example the sucrose fatty acid ester in which the monoester content is increased to 95% or more, have an HLB value of nearly 20, and they are popularly used in various fields due to the excellent and unique surfacing action owing to the high HLB thereof.

DISCLOSURE OF THE INVENTION

The present invention is to provide a lecithin surfactant superior to synthetic products in terms of safety, as one which is ready to use due to the HLB value higher than the conventional products and which has more remarkable surfactant activity.

The present invention successfully achieving the above objective is to provide a surfactant containing one or more of lysophospholipid represented by general formula;

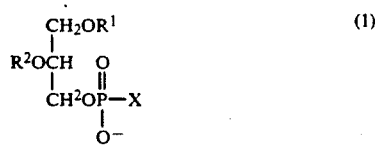

[wherein $R^1$ and $R^2$ represent hydrogen atom or the acyl residue of fatty acid, but either one of $R^1$ and $R^2$, is hydrogen atom, the other being acyl group. X represents an organic group remaining after removing one hydrogen atom of an optional hydroxyl group of polyhydric alcohol therefrom]; and to provide a method for producing the surfactant of the present invention, by treating phosphatidic acid derivative represented by

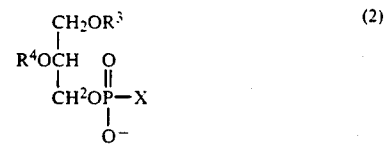

[wherein $R^3$ and $R^4$ represent the acyl residue of X represents an organic group remaining after removing one hydrogen atom of an optional hydroxyl group of polyhydric alcohol therefrom], with lipase or phospholipase $A_2$, for partial hydrolysis.

It is specifically preferable that the surfactant of the present invention is the one wherein the polyhydric alcohol corresponding to the organic group X in the general formulas (1) and (2) is ethyleneglycol, glycerol, sorbitol, mannitol, glucose, galactose, fructose, sucrose or lactose. In other words, the surfactant with the organic group corresponding to them exhibits an HLB as high as 20 or more, readily dissolves in water and exhibits excellent properties superior to those of the conventional lecithin surfactants, in terms of a great number of points such as foaming power, permeating potential, solubilizing potential, emulsifying potential and the like.

In case that the surfactant of the present invention is produced from the phosphatidic acid derivative of the general formula (2), the phosphatidic acid derivative as a material may be produced through transphosphatidylation from natural phospholipids such as soybean lecithin, egg yolk lecithin, etc., and polyhydric alcohol. Phosphatidic acid derivatives commercially available as the product name transfer lecithin, for example, phosphatidylglycerol, may be also used.

Transfer lecithin commonly contains unreacted lecithin at a high ratio, but such transfer lecithin of itself may be used as the material for the producing method according to the present invention.

As phospholipase $A_2$ to be reacted with a material compound, pancreatin derived from animal pancreas, or phospholipase $A_2$ of venom and the like may be used. In case of using phospholipase $A_2$ as the enzyme, the $\beta$ position of the material phosphatidic acid derivative is hydrolyzed, to generate lysophospholipid having a hydroxyl group at the position.

In case of using lipase as the enzyme, both or either one of $\alpha$ and $\beta$ positions of the material phosphatidic acid derivative is hydrolyzed. The reaction can be regulated by controlling the reaction condition, and it is also possible to isolate and purify the reaction products.

The multiple reaction products with different hydrolyzed positions, in a mixture, may be possibly used as a surfactant.

In case of using any enzyme, the enzyme may be used in the form of immobilized enzyme.

Suitable amounts of an enzyme and calcium ion for activating the enzyme are added to the material phosphatidic acid derivative previously suspended in water, which is then kept and reacted at about 20°-60° C. Because the enzyme activity is generally decreased at an acidic condition and it promotes degradation of materials and reaction products at pH too high, a reaction solution is appropriately at pH 7-8.5.

Since the pH of a reaction solution is lowered by released fatty acid as the reaction progresses, it is preferable during the reaction to maintain the pH within the range, by dropwise addition of alkali. The progress of the hydrolytic reaction can be estimated from the amount of the alkali added dropwise.

The reaction mixture is heated at an appropriate point to inactivate the enzyme for termination of the reaction.

The reaction solution may be used as surfactant as it is, because the reaction material is also a surfactant.

However, the solution can be treated with lyophilization or fractionation to concentrate the principal ingredient thereof, if necessary, whereby a surfactant with a remarkably enhanced activity can be obtained.

Lysophospholipid of the general formula (1), having an HLB value of 20 or more, dissolves in water more easily than known phospholipid surfacting agents, and exceeds them concerning surfacting action. The foaming power, permeating potential, solubilizing potential and the like of lysophospholipid are in the same degree as or higher than those of conventional phospholipid emulsifiers.

Lysophospholipid has excellent emulsifying potential, and concerning D-phase emulsifying potential specifically, it has even more excellent performance property than conventional products. Furthermore, it is remarkable in terms of organoleptic properties such as taste and smell.

Because the principal ingredient has the characteristic features insofar mentioned, the surfactant of the present invention is more easily usable and is excellent with a wider application field, than the conventional phospholipid surfactants.

BEST MODE FOR CARRYING OUT THE INVENTION

The present invention will be explained hereinbelow with reference to Examples.

EXAMPLE 1

Ten grams of transfer lecithin containing 84% by weight of phosphatidylglycerol (referred to as PG80, hereinafter) was suspended in 50 g of water, followed by addition of calcium chloride to 10 mM, and was adjusted to pH 8.0 with sodium hydroxide, to which was subsequently added pancreatic pancreatin (Sigma Co.) of 2000 units and reacted at 37° C. overnight. An aqueous solution of sodium hydroxide was added dropwise during the reaction that the solution might be kept at pH 8. Then, the obtained reaction solution was centrifuged and the calcium salt of the fatty acid released during the reaction was removed off as a precipitation.

The supernatant contained 89.0% by weight of lysophosphatidylglycerol where the solid concentration was 11.0% by weight and the $\beta$ position of the solids was hydrolyzed. This was subjected as a surfactant to the following performance evaluation test.

EXAMPLE 2

Following the same as in Example 1, there was produced a surfactant containing about 60% by weight of lysophosphatidylglycerol where the solid concentration was 12.0% by weight and the $\beta$ position of the solids was hydrolyzed, from transfer lecithin containing about 30% by weight of phosphatidylglycerol (referred to as PG30, hereinafter).

EXAMPLE 3

Following the same as in Example 1, except that the lipase from *Rhizopus deremer* (Seikagaku KogYo K.K.) was used as enzyme instead of pancreatin and that the pH of the reaction solution was modified to 7.0, the hydrolysis and subsequent treatment was done. The purified reaction product contained lysophosphatidylglycerol hydrolyzed at $\alpha$ position and lysophosphatidylglycerol hydrolyzed at $\beta$ position.

EXAMPLES 4–10

Using 10 g of the following transfer lecithins (each with a purity of 80% or more) as a starting material in place of the transfer lecithin (phosphatidylglycerol) in Example 1 and following the same concerning the remaining parts, surfactants composed of their corresponding lyso-type derivatives were produced.

| Example | Starting material |
|---|---|
| 4 | Phosphatidylethyleneglycol |
| 5 | Phosphatidylsorbitol |
| 6 | Phosphatidylmannitol |
| 7 | Phosphatidylglucose |
| 8 | Phosphatidylgalactose |
| 9 | Phosphatidylfructose |
| 10 | Phosphatidylsucrose |

Examples of Performance Evaluation Test

The surfactants of Examples 1 to 3, the transfer lecithins PG80 and PG30 as their materials, and the surfactants of Examples 4 to 10, were measured of their HLB, according to the actual measurement of emulsification. The surfactants of Examples 1 to 3 were also subjected to the evaluation test of surfacting action. For comparison, the same test was performed on commercially available surfactants. The added amount of the products of Examples was the added amount converted to solids. The surfactants used in Comparative Examples were as follows;

Comparative Example 1 Polyglycerin fatty acid ester MSW 750
 (Sakamoto Pharmaceutical Industry; HLB:13)
Comparative Example 2: Sucrose fatty acid ester F 160
 (Daiichi Kogyo Pharmaceuticals; HLB:15)
Comparative Example 3: Neutral Detergent Mild
 (Tamanohada Soap)
Comparative Example 4:
 Polyglycerin fatty acid ester DK ester SS (Sakamoto Pharmaceutical Industry; HLB:19)
Comparative Example 5: Polyglycerin fatty acid ester ML 500
 (Sakamoto Pharmaceutical Industry; HLB:13)
Comparative Example 6: Polyglycerin fatty acid ester ML 750
 (Sakamoto Pharmaceutical Industry; HLB:15)
Comparative Example 7: Soybean lecithin
 (Ajinomoto; HLB:6)
Comparative Example 8: Lyso-type lecithin
 (mixture of lysophosphatidylcholine and phosphatidylethanolamine; Kyowa Fermentation; HLB:12)
Comparative Example 9: Fractionated phosphatidylcholine PC 80
 (Uni-Mills; HLB:7)

1. HLB

The results of measurement are shown in Table 1.

TABLE 1

| Surfactant | HLB |
|---|---|
| PG 80 | 17.3 |
| PG 30 | 13.0 |
| Example 1 | 25.0 |

TABLE 1-continued

| Surfactant | HLB |
| --- | --- |
| Example 2 | 22.1 |
| Example 3 | 23.0 |
| Example 4 | 22.0 |
| Example 5 | 29.3 |
| Example 6 | 29.1 |
| Example 7 | 28.5 |
| Example 8 | 29.8 |
| Example 9 | 27.0 |
| Example 10 | 30.2 |

Permeating potential

Canvas of a 2 cm diameter (Canvas Disk #6) is gently placed on an aqueous sample solution of 0.25% concentration.

When the canvas gets wet to purge air from the cloth, the disk sinks. The time required to make the disk sink below the water surface is measured to indicate the permeating potential (The shorter the time required until the precipitation, the more intense the permeating potential is.

In case that the precipitation time is within 20 minutes, the measurement is repeated five times, thereby determining a mean value of three measured values excluding the longest and the shortest ones. If the time is 20 min–30 min, determine a mean value of two measured values. The time 30 minutes or more is not measured.)

The results of measurement are shown in Table 2.

TABLE 2

| Surfactant | Time until precipitation |
| --- | --- |
| Comparative Example 1 | 30 min or more |
| Comparative Example 3 | 10 min 39 sec |
| Comparative Example 4 | 30 min or more |
| Comparative Example 5 | 5 min |
| Comparative Example 6 | 4 min 55 sec |
| Comparative Example 7 | 30 min or more |
| Comparative Example 8 | 8 min 52 sec |
| Comparative Example 9 | 30 min or more |
| PG 80 | 25 min 35 sec |
| PG 30 | 21 min 14 sec |
| Example 1 | 2 min 37 sec |
| Example 2 | 3 min 50 sec |
| Example 3 | 3 min 33 sec |

3. Foaming power

An aqueous 0.2% sample solution of 5 ml is placed in a tube with screw cap and is stirred at 67 times/min for five minutes. The height of foam is measured, immediately and 1 hour after.

The results of measurement are shown in Table 3.

TABLE 3

| Surfactant | Immediately after stirring | One hour after stirring |
| --- | --- | --- |
| Comparative Example 2 | 13 | 12 |
| Comparative Example 6 | 41 | 38 |
| PG 80 | 21 | 13 |
| PG 30 | 3 | — |
| Example 1 | 36 | 34 |
| Example 2 | 3 | — |
| Example 3 | 29 | 20 |

4. D-phase emulsifying potential (emulsification of O/D type)

When an emulsifying agent is dissolved in polyhydric alcohol at a high concentration and oil is then added, the oil may eventually be incorporated in the state of transparent solution. When the transparent solution is introduced into water, the oil is dispersed in water after being turned into extremely fine particles, whereby a stable oil-in-water emulsion can be easily obtained without using mechanical power. This is D-phase emulsion. Quillaia saponin is remarkable in terms of D-phase emulsifying potential and is in practical use for emulsifying perfume.

Regarding the products of Examples and quillaia saponin Quillaianin C-100 (Maruzen Kasei K.K.), the D-phase emulsifying potential in their formulas hereinbelow described was investigated.

TABLE 4

| Material | Formula | | | |
| --- | --- | --- | --- | --- |
| | A | B | C | D |
| Emulsifying agent | 0.08 | 0.08 | 0.10 | 0.50 |
| Isomerized sugar (Bx73.6) | 17 | — | 64 | 64 |
| Water | 1.5 | 2 | 2 | — |
| Sorbit (75%) | — | 17 | — | — |
| Rapeseed oil | 55 | 56 | — | — |
| Orange oil | — | — | 20 | 20 |

The results of the test are as follows:

Formula A: Only Example 1 succeeded in D-phase emulsion.

Formula B: Only Example 1 succeeded in D-phase emulsion.

Formula C: Only Example 1 succeeded in D-phase emulsion.

Formula D: Examples 1 to 3 and Quillaianin C-100 succeeded in D-phase emulsion.

What is claimed is:

1. Surfactant containing one or more lysophospholipid represented by the general formula;

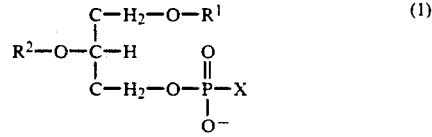

(1)

wherein $R^1$ and $R^2$ represent a hydrogen atom or the acyl residue of a fatty acid, but either one of $R^1$ and $R^2$ is a hydrogen atom, the other is an acyl group; X represents an organic group remaining after removing one hydrogen atom of an arbitrarily selected hydroxyl group of a polyhydric alcohol selected from the group consisting of ethyleneglycol, glycerol, sorbitol, mannitol, glucose, galactose, fructose, sucrose and lactose.

2. A method for producing a surfactant comprising treating a phosphatidic acid derivative represented by the following formula

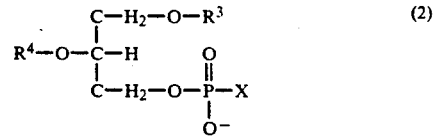

(2)

with lipase or phospholipase $A_2$ for partial hydrolysis, wherein $R^3$ and $R^4$ represent the acyl residue of a fatty acid, and X represents an organic group remaining after removing one hydrogen atom of an arbitrarily selected hydroxyl group of a polyhydric alcohol selected from the group consisting of ethylenglycol, glycerol, sorbitol, mannitol, glucose, galactose, fructose, sucrose and lactose.

3. The method for producing a surfactant according to claim 2, wherein the phosphatidic acid derivative comprises a material transfer lecithin in which the base bonded with a phosphoryl group of natural phospholipid is substituted with the polyhydric alcohol.

4. The method for producing a surfactant according to claim 2, wherein the phospholipase $A_2$ is pancreatin derived from animal pancreas and/or phospholipase $A_2$ of venom and the like.

5. The method for producing a surfactant according to claim 2, wherein the phosphatidic acid derivative is hydrolyzed at $\beta$ position by said phospholipase $A_2$.

6. The method for producing a surfactant according to claim 2, wherein the phosphatidic acid derivative is hydrolyzed at $\alpha$ or $\beta$ positions with lipase.

7. The method for producing a surfactant according to claim 2, wherein the reaction solution in the hydrolysis of said phosphatidic acid derivative is at pH 7 to 8.5.

8. The method for producing a surfactant according to claim 2, comprising adding an appropriate amount of calcium ion to the reaction solution in the hydrolysis of said phosphatidic acid derivative.

* * * * *